United States Patent [19]
Menut et al.

[11] Patent Number: 5,928,241
[45] Date of Patent: Jul. 27, 1999

[54] QUICK CONNECTION METHOD AND DEVICE, AND SURGICAL INSTRUMENT FOR DRIVING INTERCHANGEABLE ROTARY TOOLS

[75] Inventors: Jean-Baptiste Menut, Geneva; Pierre Pahud, Lausanne, both of Switzerland

[73] Assignee: Sodem Diffusion S.A., Geneva, Switzerland

[21] Appl. No.: 08/973,400

[22] PCT Filed: Jun. 14, 1996

[86] PCT No.: PCT/CH96/00228

§ 371 Date: Dec. 12, 1997

§ 102(e) Date: Dec. 12, 1997

[87] PCT Pub. No.: WO97/00149

PCT Pub. Date: Jan. 3, 1997

[30] Foreign Application Priority Data

Jun. 14, 1995 [CH] Switzerland ............................ 1752/95

[51] Int. Cl.$^6$ ........................................................ A61B 17/00
[52] U.S. Cl. .............................. 606/80; 606/180; 279/22; 279/143
[58] Field of Search .................................. 606/79, 80, 81, 606/86, 167–180; 279/22, 24, 30, 75, 143, 145

[56] References Cited

U.S. PATENT DOCUMENTS

| | | | |
|---|---|---|---|
| 922,602 | 5/1909 | Lamb | 279/22 |
| 2,751,229 | 6/1956 | Schultz | 279/24 |
| 3,867,943 | 2/1975 | Nordin | 408/283 |
| 5,271,697 | 12/1993 | Johnson et al. | |
| 5,720,749 | 2/1998 | Rupp | 606/79 |
| 5,741,263 | 4/1998 | Umber et al. | 606/80 |
| 5,779,404 | 7/1998 | Jore | 279/81 |

FOREIGN PATENT DOCUMENTS

| | | |
|---|---|---|
| 1424002 | 3/1966 | France . |
| 8712362 | 11/1988 | Germany . |
| 8901367 | 6/1989 | Germany . |
| 512954 | 11/1971 | Switzerland . |
| 573743 | 3/1976 | Switzerland . |
| 575229 | 5/1976 | Switzerland . |
| 664516 | 3/1988 | Switzerland . |
| 671174 | 8/1989 | Switzerland . |

OTHER PUBLICATIONS

Copy of an International Search Report in PCT/CH96/00228.

*Primary Examiner*—Daniel W. Howell
*Assistant Examiner*—Rouzbeh Tabaddor
*Attorney, Agent, or Firm*—Greenblum & Bernstein P.L.C.

[57] ABSTRACT

The present invention relates to a quick connection device for driving various rotary tools by use of a drive shaft surrounded by a housing. Each tool includes a shank with a groove and a coupling projection. A rotary tool holder tube is mounted on bearings in a supporting tube and is provided with a first quick connection snap coupling which includes balls surrounded by a resilient sleeve and which are capable of engaging the groove in the tool shank. The shank is coupled to the drive shaft by the coupling projection and a slot in the drive shaft. Engagement of the second quick connection coupling joining the supporting tube to the housing simultaneously blocks the resilient sleeve. The quick connection coupling device is used in a surgical instrument which enables a variety of rotary cutting tools to be operated at varying distances from the drive shaft by use of a set of intermediate spindles of various lengths having the same structure as the quick connection device. When the second coupling device is engaged, a movable coupling member surrounds the resilient sleeve and locks the balls in the groove in the tool shank. The surgical instrument is provided with a set of tools with identical shanks that fit the tool holder tube and include the groove and coupling projection. The instrument is particularly suitable for use in orthopedic surgery.

16 Claims, 1 Drawing Sheet

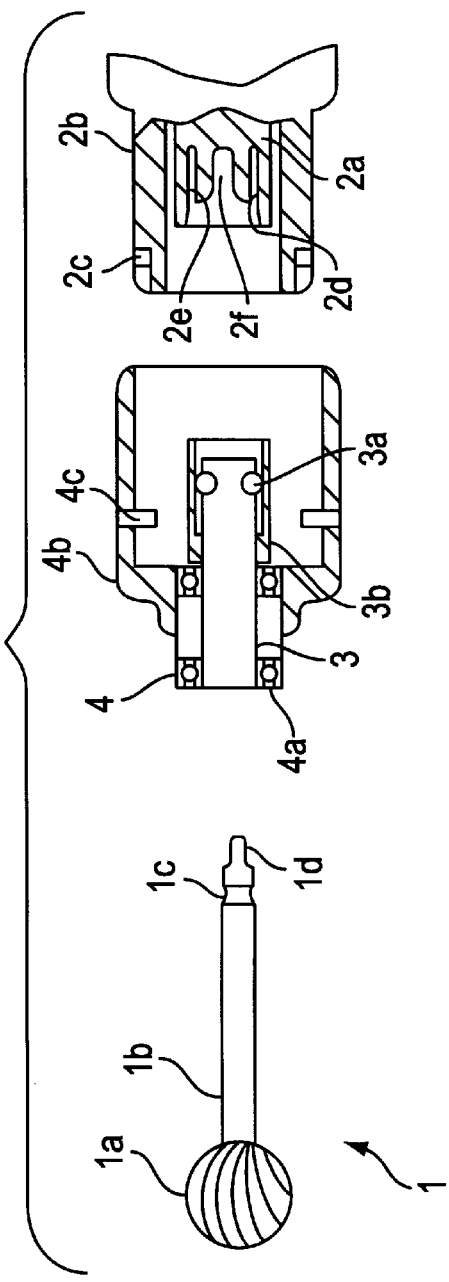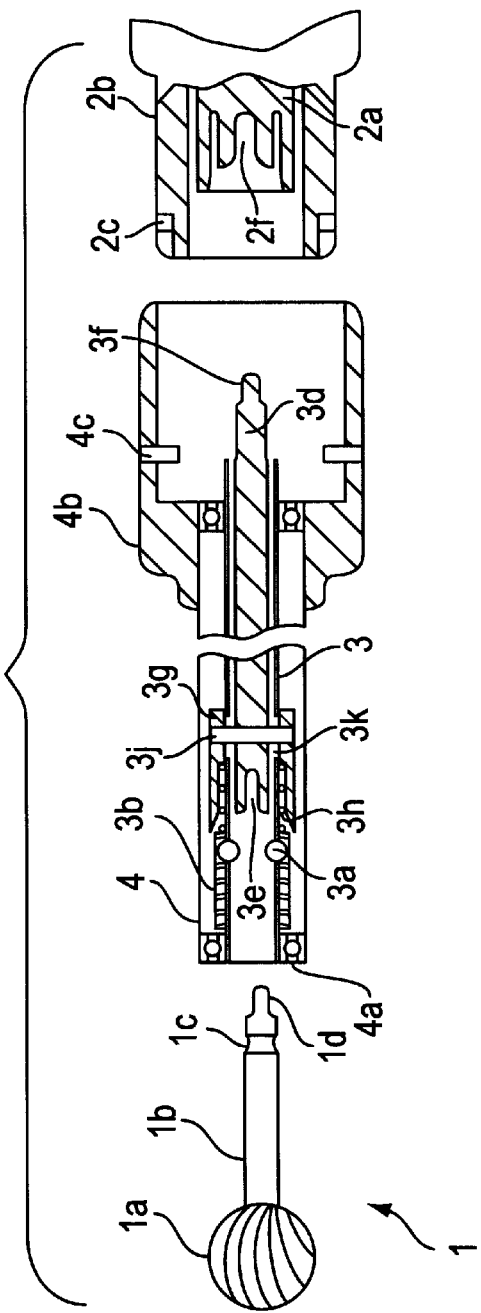

5,928,241

QUICK CONNECTION METHOD AND DEVICE, AND SURGICAL INSTRUMENT FOR DRIVING INTERCHANGEABLE ROTARY TOOLS

CROSS-REFERENCE TO RELATED APPLICATIONS

The present application is a National Stage under 35 U.S.C. §371 of PCT/CH96/00228 and claims priority of Swiss Patent Application No. 1752/95-6 filed Jun. 14, 1995.

CROSS-REFERENCE TO RELATED APPLICATION

1. Field of the Invention

The invention relates to the quick connection of interchangeable tools to a drive shaft and in particular to a surgical instrument for driving interchangeable tools at different predetermined distances from the drive shaft.

2. Discussion of Background Information

Various surgical instruments currently used to drive various interchangeable tools at different distances from a drive shaft are provided with a first set of special tools and a second set of guide spindles having a length which varies according to the required distance from case to case between the cutting head and the drive shaft.

These known instruments provide for first connecting each special tool to the drive shaft by means of a collet chuck and then screwing each guide spindle onto a housing surrounding the drive shaft. These chucking and screwing actions are moreover carried out with the help of two special keys for ensuring an adequate connection of the tools to the drive shaft, and entail a waste of time required to replace the tools.

Said instruments must moreover be provided with a considerable number of special tools, this number being equal to the number of types of cutting heads required, multiplied by the number of lengths required to ensure the different distances between the cutting heads and the drive shaft. Now, this can entail considerable tooling costs as well as stocking problems, since it is advisable to always keep an adequate stock of these special tools of different types and lengths which are relatively expensive and wear out more or less rapidly depending on the amount of use made of the various tools.

The art relating to tool connection devices comprising self-clamping and locking means may be illustrated by the following patents.

CH 575 229 concerns a surgical drill comprising a drive shaft in a first casing, a removable head provided with a driven shaft in a second casing, a cutting tool which may be coupled with said driven shaft, a clutch member fixed to the drive shaft and a clamping jaw fixed to said driven shaft, which come into the driving position when said casings are connected.

CH 573 743 concerns a surgical drill comprising a drive shaft in a housing, an intermediate driven shaft coupled with the drive shaft mounted in a rear housing coupled with the housing of the drive shaft and connected by a gearing to a front driven shaft associated with a tool fastening device and CH 671 174 concerns a self-clamping chuck intended to eliminate the drawbacks of the necessity of using a chuck key in portable instruments currently employed for surgical use.

CH 512 954 concerns a device for locking tools on a mandrel and CH 664 516 relates to a locking device for locking a tool in a rotor.

The known tool connection devices and surgical instruments mentioned above moreover do not fully meet all the strictest requirements regarding the rapidity, structural simplicity and reliability of the technical means employed, without help of a key or other auxiliary tool.

OBJECT OF THE INVENTION

An object of the invention is to provide a device for quick connection of interchangeable tools and more particularly a surgical tool comprising such a connection device which allows the mentioned drawbacks of the known connection devices and instruments to be obviated and has a structure which is as simple, compact and reliable as possible, so as to enable the connection and locking of a plurality of interchangeable rotary cutting tools to be ensured in the shortest possible time and without requiring the help of any auxiliary means, and so as to more particularly enable the cutting tools to be operated at different predetermined distances from the drive shaft.

SUMMARY OF THE INVENTION

The present invention as defined in the claims relates to a quick connection method and device for interchangeable tools and to a surgical instrument provided with such a connection device and specially intended for driving interchangeable tools at different distances from a drive shaft.

The present invention ensuring the quick connection of various interchangeable rotary tools to a motor by means of a combination of simple and reliable means comprising:

(a) standard tools having identical shanks whose diameter is adapted to a rotary tool holder tube mounted in a supporting tube, (b) a first quick connection device which ensures fixing the tool in the tool holder tube, (c) a second quick connection device enabling mounting the supporting tube on the housing of the drive shaft, (d) means for coupling the shank of the tool with the drive shaft and (e) locking means enabling the first quick connection device to be locked and released when the second quick connection device is respectively engaged or disengaged.

BRIEF DESCRIPTION OF THE DRAWINGS

The present invention is further described in the detailed description which follows: in reference to the noted plurality of drawings by way on non-limiting examples of preferred embodiments of the present invention, in which like reference numerals represent similar parts throughout the several views of the drawings, and wherein:

FIG. 1 is a longitudinal sectional view of an embodiment of a quick connection device according to the invention associated with a tool and a drive shaft.

FIG. 2 is a longitudinal sectional view of an embodiment of a surgical instrument comprising a quick connection device according to the invention associated with a tool and a drive shaft.

DETAILED DESCRIPTION OF THE PRESENT INVENTION

The particulars shown here are by way of example and for purposes of illustrative discussion of the embodiments of the present invention only and are presented in the cause of providing what is believed to be the most useful and readily understood description of the principles and conceptual aspects of the present invention in more detail than is necessary for the fundamental understanding of the present invention, the description taken with the drawings making apparent to those skilled in the art how the several forms of the present invention may be embodied in practice.

FIG. 1 shows a quick connection device according to the invention for driving an interchangeable rotary cutting tool 1 by means of a drive shaft 2a which is provided with a coupling slot 2f and is mounted in a housing 2b provided with a locking groove 2c.

The cutting tool 1 associated with this connection device comprises a cutting head 1a integral with a round shank 1b which has a predetermined diameter and length and is provided with an annular groove 1c and a coupling projection 1d.

The form and dimensions of the cutting tool 1, the drive shaft 2a and its housing 2b are adapted to the connection device.

The quick connection device according to the invention essentially comprises a rotary tool holder tube 3 mounted coaxially in a supporting tube 4 and arranged in bearings 4a so as to rotate freely around the common axis of these tubes 3 and 4.

The diameter of the tool holder tube 3 is chosen so as to be slightly larger than the diameter of the shank 1b and to enable guiding and mounting the cutting tool 3 in this tube 3 with a slight clearance. The required distance between the cutting head 1a and the drive shaft 2a is determined by the length of this tube 3. This length is in this case adapted to the length of the tool shank 1b so that the coupling projection 1d of this shank 1b protrudes at the rear end of the tube 3 when the tool is mounted in this tube.

A first quick connection device serving to mount the tool in the tool holder tube 3 here comprises two radially movable balls 3a which are seated in two diametrically opposite holes in this tube 3 and are kept in place in these holes by an elastic split sleeve 3b fixedly mounted on the tool holder tube 3.

Thus, as appears from FIG. 1, the balls 3a normally enter into the tool holder tube 3 due to the action of the sleeve 3b, while they are engaged in the groove 1c of the shank 1b when the tool is mounted in this tool holder tube 3. Its coupling projection 1d then protrudes from the rear end of this tool holder tube 3 in order to enable engagement of this projection 1d in the coupling slot 2f of the drive shaft 2a. The drive shaft 2a is provided with an annular cavity 2d defined by an annular outer wall 2e and dimensioned so as to be able to receive the rear portion of the elastic sleeve 3b therein.

The coupling slot 2f is in this case adapted to the coupling projection 1d so that the cutting tool is directly coupled with the shaft 2a when the projection 1d is engaged in the slot 2f of the drive shaft.

A second quick connection device associated with the supporting tube 4 and the housing 2b of the drive shaft 2a in this case consists of a socket joint of the bayonet type comprising a sleeve 4b which is solid with this tube 4 at its rear end and is provided with two inner diametrically opposite locking pins 4c. This sleeve 4b thus forms the female part or socket of said second quick connection device of the bayonet type. The housing 2b of the drive shaft 2a has two locking grooves 2c and it is adapted to the sleeve 4b so that it constitutes the male part of the second connection of the bayonet type.

The described connection device represented in FIG. 1 ensures mounting and removal of the interchangeable tools to be effected in two very simple and rapid stages.

The required cutting tool is first connected to the tool holder tube 3 in a very brief first stage which simply consists in thrusting the shank 1b into the front end of this tube 3 until the movable balls 3a engage in the groove 1c of the tool shank and the projection 1d of this shank protrudes from the rear end of the tool holder tube 3.

Axial displacement of the shank 1b now drives the balls 3a outwards from this tube 3, while they are then driven radially inwards by the sleeve 3b and finally engage in the groove 1c of the shank 1b, thereby preventing any axial displacement of the shank 1b. The projection 1d of the tool shank 1b protruding from the rear end of the tool holder tube 3 in this case enables coupling tool 1 at the same time as the tool holder tube 3 with the drive shaft 2a.

The supporting tube 4 is then connected to the housing 2b of the drive shaft 2a in a very brief second stage which simply consists in passing the housing 2b of the drive shaft 2a through the bayonet socket 4b of the supporting tube 4 so that the pins 4c are displaced backwards in the locking grooves 2d and ensure locking by carrying out a relative rotation therein. This second connection at the same time ensures coupling of the tool 1 and the tool holder tube 3 with the shaft 2a due to engagement of the projection 1d of the tool in the slot 2f of the shaft 2a.

The rear end of the elastic sleeve 3b is thus made to engage in the annular cavity 2d of the shaft 2a and the annular wall 2e is brought to surround this elastic sleeve 3b, thus ensuring that the balls 3a are caught in the groove 1c of the tool and consequently locking the tool in the tube 3.

FIG. 2 shows an embodiment of a surgical instrument provided with a quick connection device according to the invention comprising an intermediate spindle having a structure which is specially designed to enable the quick and reliable connection of interchangeable tools 1 at several predetermined distances from the drive shaft associated with this instrument.

The surgical instrument provided with the connection device shown in FIG. 2 enables any number of interchangeable tools having identical shanks and various required cutting heads to be advantageously combined with any number of interchangeable intermediate spindles having the same structure and the different lengths required to modify the distance between the tool and the drive shaft from case to case. FIG. 2 represents a single cutting tool and a single intermediate spindle, whose structure described hereinafter is essentially the same for all of the tools, and the intermediate spindles which may be used in various combinations of tools and spindles within the scope of the invention.

The surgical instrument represented in FIG. 2 serves to drive a cutting tool 1 by means of a quick connection device which essentially comprises an intermediate spindle consisting of a rotary tool holder tube 3 mounted in a supporting tube 4 by means of bearings 4a. The tool holder tube 3 is provided with balls 3a and an elastic sleeve 3b arranged in the manner already described with reference to FIG. 1.

A movable coupling part 3d is mounted in this rotary tool holder tube 3, has an intermediate coupling slot 3e arranged to receive the coupling projection 1d of the tool when the latter is mounted in the tube 3 and it is further provided with a coupling projection 3f which protrudes from the rear end of the tool holder tube 3 and is adapted to engage the coupling slot 2f of the drive shaft 2a.

As further appears from FIG. 2, a movable locking sleeve 3g is arranged on the tool holder tube 3, is separated from the elastic sleeve 3b by a pressure spring 3h and is fastened to the mobile coupling part 3d by means of a pin 3j passing through two opposite longitudinal slots 3k recessed in the tube 3.

Said intermediate spindle is further associated with a second quick connection device consisting of a socket joint of the bayonet type comprising the following elements already described with reference to FIG. 1: the sleeve 4b with the pins 4c, constituting the socket or female element of this second quick connection device, and the housing 2b with the locking groove 2c, constituting the male element of the second quick connection device.

As far as the action of the described connection is concerned, the tool 1 is at first mounted at the front end of the tube 3 by inserting the shank 1b so that it pushes aside the balls 3a out against the action of the elastic sleeve 3b so as to enable axial displacement of this shank 1b until the coupling projection 1d is engaged in the coupling slot 3e of the intermediate coupling part 3d, the balls then being driven inwards by the split sleeve and engaged in the groove 1c and the tool thus being correctly positioned and coupled with the tool holder tube 3 by means of the coupling part 3d.

The supporting tube 4 is then connected to the housing 2b of the shaft 2a by means of said bayonet connection, the tool holder tube 3 being coupled at the same time with the drive shaft 2a. Thus, when the housing 2b is inserted into the connecting sleeve 4b of the supporting tube 4, the projection 3f of the intermediate coupling part 3d is engaged in the slot 2f of the drive shaft 2a and comes to abut against the bottom of this slot 2f.

Consequently, the connection of the intermediate spindle to the housing 2b surrounding the drive shaft 2a brings about a displacement of the intermediate coupling part 3d and thus causes the displacement of the locking sleeve 3g against the action of the pressure spring 3h so that this sleeve 3g is made to surround the elastic sleeve 3b. One thus prevents any expansion of this split sleeve 3b, thus ensuring that the balls 3a are caught in the groove 1c of the tool.

One thus obtains a solid connection of all the rotary elements (tool 1, tool holder tube 3, part 3d, drive shaft 2a) on one hand and the fixed elements (supporting tube 4, housing 2b) on the other hand.

The described instrument is advantageously provided according to the invention with a plurality of cutters of different types all of the same length, a plurality of intermediate spindles having different lengths and quick connection device and locking means enabling said cutters to be mounted selectively at predetermined distances from the drive shaft by means of said spindles.

One thus requires for this instrument only one set of cutters of the same length and different types which may be mounted selectively on said intermediate spindles of different lengths in order to carry out all the surgical interventions required from case to case.

Due to the use of a set of said intermediate spindles, it becomes possible to fix any cutter to any intermediate spindle and to reduce the number of cutters of equal length to the number of required cutter types The quick connection device and locking of each cutter are ensured by particularly simple and reliable technical means which are specially provided in accordance with the invention so that the fastening and locking functions are decoupled.

Thus, in the described embodiments, mounting each cutter on a spindle of predetermined length is first ensured by a spring snap coupling, while locking of the snap coupling is activated when the spindle is then mounted on the housing of the drive shaft.

In the described embodiments, the snap coupling and locking the cutter only ensure longitudinal fixing of the cutter, while rotation of the cutter is ensured by projections and slots associated with the cutter and the drive shaft.

It is nevertheless conceivable that the snap coupling locking function may simultaneously ensure the cutter driving function, for example by a clamp actuated by the locking mechanism.

It is essential for the snap coupling of the cutter to be obtained by hand when the spindle supporting tube is not mounted on the drive shaft housing, for the operator to be able to actually feel when the cutter is correctly set in place, and for locking the snap coupling to be achieved when the spindle is mounted on the drive motor housing.

Advantages

The special combination of features provided for according to the invention allows a particular combination of various practical advantages to be achieved, which may be explained as follows.

The connection as well as replacement of the tools is obtained in a safe manner in the shortest time possible, without any auxiliary tool.

A large variety of combinations of cutter types and instrument lengths can be ensured, while limiting the required number of cutters to the strict minimum. Thus, for example, a motor provided with 6 types of cutters of equal length and with 3 intermediate spindles of different lengths enables the choice of 18 combinations of cutter types and instrument lengths.

This enables on one hand considerable savings in the tooling costs in comparison with known instruments, which would require 18 cutters of six different types and 3 different lengths, as well as 3 spindles of different lengths in this particular case given by way of example.

It is noted that the foregoing disclosure has been provided merely for the purpose of explanation and is in no way to be construed as limiting of the present invention. While the present invention has been described with reference to a preferred embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

We claim:

1. A method for quick connection of interchangeable rotary tools to a drive shaft mounted in a housing having a free open end, comprising:

(a) fixing standard tools having cutting heads of an appropriate shape to identical round shanks having a predetermined length and diameter, (b) creating a slight clearance between the diameter of said shanks and a rotary tool holder tube so that said shanks can slide in a tool supporting tube, (c) changing a length of said tool holder tube to a predetermined length between the drive shaft and the cutting heads of each tool mounted in said tool holder tube, (d) mounting said tool holder tube coaxially in a fixed supporting tube so that said tool holder tube freely rotates in said supporting tube, (e) providing said tool holder tube and said shanks of said standard tools with a first quick connection device which enables fixing an axial position of said shank in said tool holder tube, (f) providing a second quick connection device with said supporting tube and said housing, (g) providing a coupling with the shank of each of said tools and with the drive shaft, which enables coupling said shank with said drive shaft, (h) providing a locking mechanism with said first quick connection device and said second quick connection device, which enables locking and releasing said first quick connection device when said second quick connection device is respectively engaged and disengaged, (i) connecting each of said tools to said tool holder tube by means of said first quick connection device by inserting the shank of said tools into said tool holder tube, (j) connecting said supporting tube to said housing by means of said second quick connection device, while effecting coupling of the shaft of the tool mounted in said tool holder tube with said drive shaft and at the same time effecting locking of said second connection device as well as said first quick connection device so as to make said tool unitary with said rotary tool holder tube and said drive shaft and to further enable releasing said tool as soon as said second quick connection device is disengaged.

2. A device for quick connection of interchangeable rotary tools to a drive shaft, comprising:

(a) a rotary tool holder tube mounted coaxially on a supporting tube;

(b) a first quick connection device comprising a fastening mechanism connecting a tool to said tool holder tube;

(c) a coupling mechanism coupling said drive shaft with said tool;

(d) a second quick connection device associated with said supporting tube and with a housing disposed around the drive shaft; and (e) a lock mechanism associated with said tool holder tube and with said drive shaft so as to cause locking of said first quick connection device by means of said second quick connection device.

3. The quick connection device according to claim 2, wherein said first quick connection device comprises a snap coupling enabling a tool to be inserted and fixed in said tool holder tube as well as to be quickly released to enable replacement of said tool.

4. The quick connection device according to claim 3, wherein said first quick connection device comprises two movable balls seated in holes recessed in said tool holder tube and associated with an elastic sleeve fixed on said tool holder tube so that said balls are kept in an inner position wherein said balls enter into said tool holder tube in order to fix the tool and said balls being moveable outwardly to liberate the tool.

5. The quick connection device according to claim 3, wherein a diameter of said tool holder tube is adapted to interchangeable tools comprising a round shank having a diameter enabling said interchangeable tool to be mounted in said tool holder tube with a slight clearance, an annular groove associated with said snap coupling and a coupling projection.

6. The quick connection device according to claim 2, wherein said second quick connection device is provided as a socket joint, ends of said housing of the drive shaft and of the supporting tube to be connected therewith being arranged so as to constitute male and female parts of said socket joint.

7. The quick connection device according to claim 6, wherein an end of the supporting tube connectable to said housing of the drive shaft is provided with a sleeve constituting the female part and said housing is arranged so as to constitute the male part of said socket joint.

8. A surgical instrument provided with a quick connection device arranged to drive interchangeable cutting tools at different predetermined distances from a drive shaft, wherein:

(a) said instrument is provided with a set of interchangeable intermediate spindles connected with a set of interchangeable tools provided with identical shanks, said spindles each having a length which corresponds to a predetermined distance between each of said tools and said drive shaft, each of said spindles comprising a rotary tool holder tube mounted in a supporting tube and said interchangeable tools having cutting heads of different forms and identical shanks having a predetermined diameter and length, (b) said tool holder having an inner diameter enabling insertion of said shank of each of said tools with a slight clearance, a first quick connection device being associated with said tool holder tube so as to enable fastening each of said tools and coupling means being provided so as to enable coupling said tools with the drive shaft by means of said tool holder tube, (c) said supporting tube associated with a second quick connection device so as to fix said supporting tube to said housing, and (d) said first and second quick connection devices being provided with a lock mechanism so that locking of said first quick connection device is ensured by said second quick connection device to thereby ensure fixing said tools, while separation of said second quick connection device enables releasing of said tools.

9. A surgical instrument according to claim 8, wherein said second quick connection device comprises a snap coupling enabling inserting and fixing said tools in said tool holder tube as well as quick release of said tools.

10. A surgical instrument according to claim 9, wherein said first quick connection device comprises movable balls seated in holes recessed in said tool holder tube and associated with an elastic sleeve fastened to said tool holder tube and arranged so as to keep said balls in an inner position wherein said balls enter into said tool holder tube to enable fastening said tools and so that said balls may be driven outwards to release said tools.

11. A surgical instrument according to claim 9, including a set of interchangeable tools comprising identical round shanks which have a diameter enabling said tools to be mounted with a slight clearance in said tool holder tube, an annular groove being provided with said snap coupling and a coupling projection.

12. The quick connection device according to claim 4, wherein a diameter of said tool holder tube is adapted to interchangeable tools comprising a round shank having a diameter enabling said interchangeable tool to be mounted in said tool holder tube with a slight clearance, an annular groove associated with said snap coupling and a coupling projection.

13. The quick connection device according to claim 3, wherein said second quick connection device is provided as a socket joint, ends of said housing of the drive shaft and of the supporting tube to be connected therewith being arranged so as to constitute male and female parts of said socket joint.

14. The quick connection device according to claim 4, wherein said second quick connection device is provided as a socket joint, ends of said housing of the drive shaft and of the supporting tube to be connected therewith being arranged so as to constitute male and female parts of said socket joint.

15. The quick connection device according to claim 5, wherein said second quick connection device is provided as a socket joint, ends of said housing of the drive shaft and of the supporting tube to be connected therewith being arranged so as to constitute male and female parts of said socket joint.

16. A surgical instrument according to claim 9 including a set of interchangeable tools comprising identical round shanks which have a diameter enabling said tools to be mounted with a slight clearance in said tool holder tube, an annular groove being provided with said snap coupling and a coupling projection.

* * * * *